United States Patent [19]

Beu

[11] 4,330,277
[45] May 18, 1982

[54] DENTAL FACE BOW

[75] Inventor: Richard A. Beu, Eggertsville, N.Y.

[73] Assignee: Teledyne Hanau, Buffalo, N.Y.

[21] Appl. No.: 133,495

[22] Filed: Mar. 21, 1980

[51] Int. Cl.³ .............................................. A61C 19/04
[52] U.S. Cl. ...................................................... 433/73
[58] Field of Search ........................................... 433/73

[56] References Cited

U.S. PATENT DOCUMENTS

| | | | |
|---|---|---|---|
| 1,052,806 | 2/1913 | Evans | 433/73 |
| 1,188,416 | 6/1916 | Dalbey | 433/73 |
| 1,402,225 | 1/1922 | Garretson | 433/73 |
| 1,497,259 | 6/1924 | Bonoff | 433/73 |
| 2,794,253 | 6/1957 | Fitzsimmons | 433/73 |
| 3,084,438 | 4/1963 | Goodfriend | 433/73 |
| 3,130,494 | 4/1964 | McKay | 433/73 |
| 3,218,716 | 11/1965 | Stuart | 433/73 |
| 4,084,319 | 4/1978 | Dragan | 433/73 |
| 4,261,696 | 4/1981 | Hobo | 433/73 |

OTHER PUBLICATIONS

"New Denar Slidematic Face Bow", by Denar Corp., 901 E. Cerritos, Anaheim CA 92805.
"Instructions for the Use of the Whip-Mix Articulator and Quick Mount Face Bow", by Whip-Mix Corp., 361 Farmington Ave., Louisville, KY 40217.
"Hanau Arcon H2 Series Articulators", by Teledyne Hanau, 80 Sonwil Drive, Buffalo, NY 14225.
"Hanau PRI Facebows", by Hanau Engr. Co. Inc., 3 (pp.) and Technical Sheet Facebows and Earpiece Facebow, p. 15, by Hanau Engr. Co. INc., Buffalo, NY 14225.

Primary Examiner—Robert Peshock
Attorney, Agent, or Firm—Raymond F. Kramer

[57] ABSTRACT

A dental face bow which is readily fittable to a patient's head includes a pair of contact members, such as ear pieces, to be positioned against aural-temporal areas, such as external auditory meatuses, on opposite sides of the patient's head, members to support the contact members, a threaded moving device, which is a thumb wheel operated telescoping unit, for simultaneously moving the supporting members and the contact members nearer together or farther apart, as desired, in a straight line path, in response to rotation of a part of the moving device, e.g., the thumb wheel and auxiliary telescoping means joined to the supporting members for the ear pieces and parallel to the threaded telescoping means, to prevent relative movement of the supporting members. The face bow is adapted to have joined to it universally adjustable mounting means, including a transfer rod, on which a bite index, including a bite plate, may be mounted, which transfer rod, together with the bite index held thereto, is removable from the face bow and readily transferable to a dental articulator in desired bite plate position to aid in mounting a maxillary dental cast.

Also described are: particular types of ear pieces; finger pieces on the face bow to enable a patient to assist in fitting the face bow to his head; means for holding an orbitale pointer in desired storage position on the face bow when the pointer is not in use; an improved transfer rod, including improved means for selectively fastening it to a face bow and to a dental articulator and improved means for assisting in positioning the transfer rod for such fastenings; and an improved universal mounting jig for readily mounting on any of a variety of articulators a bite and transfer rod combination in desired position corresponding to that on the face bow.

7 Claims, 14 Drawing Figures

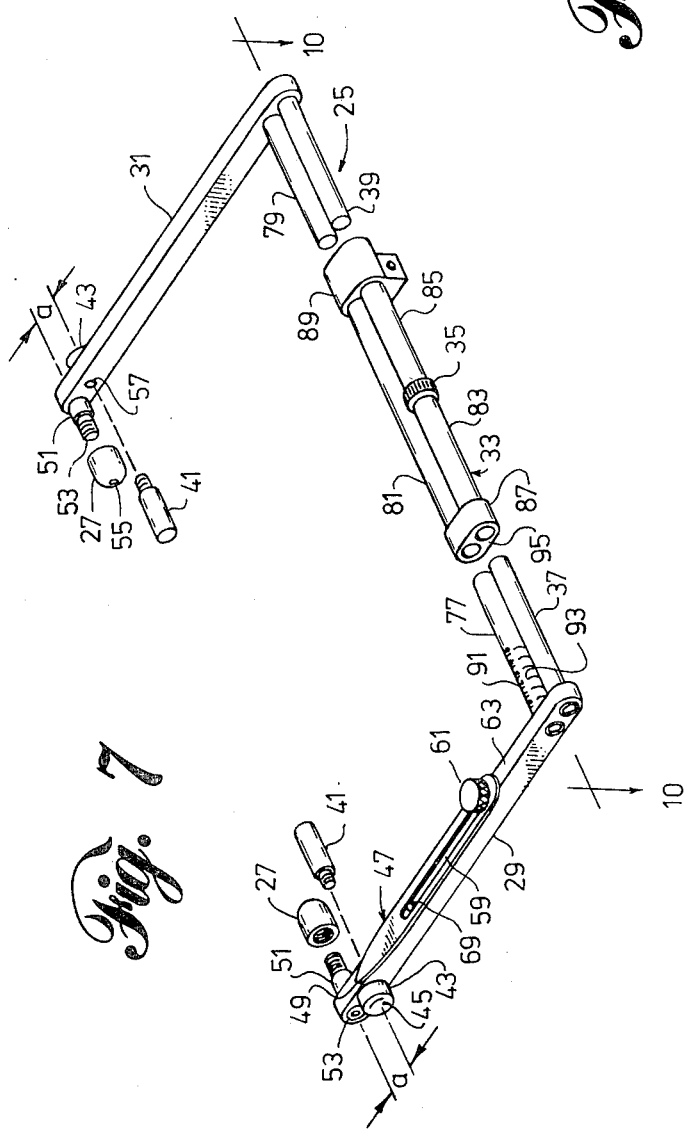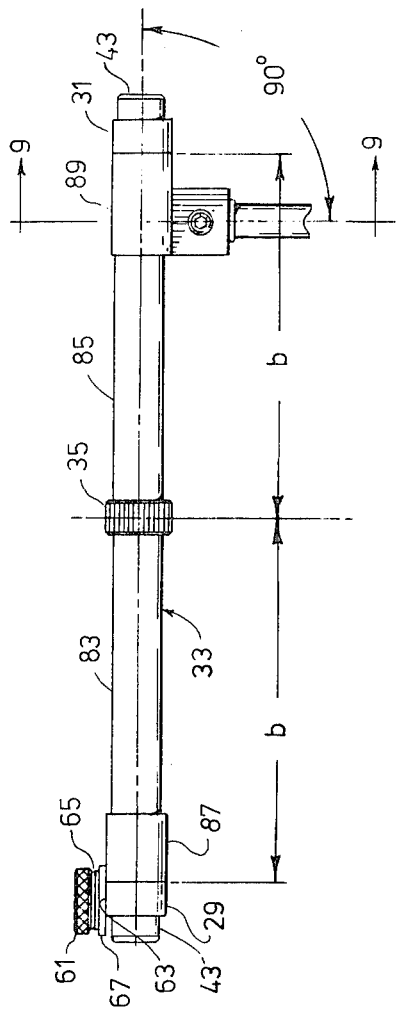

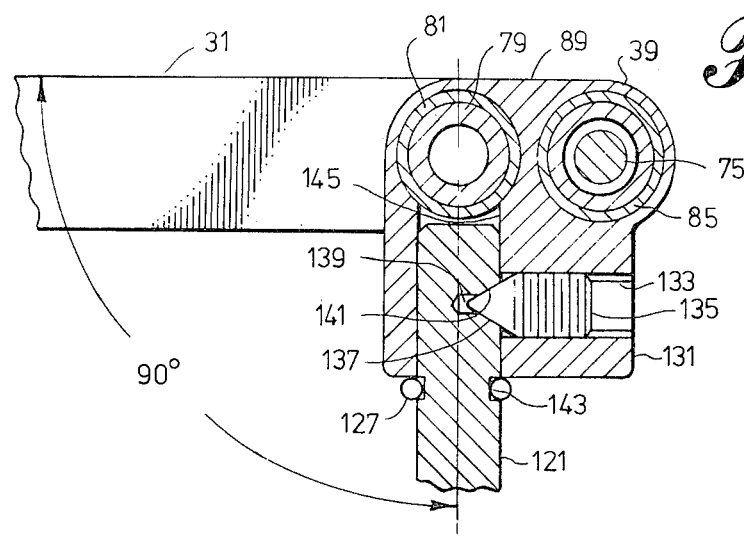
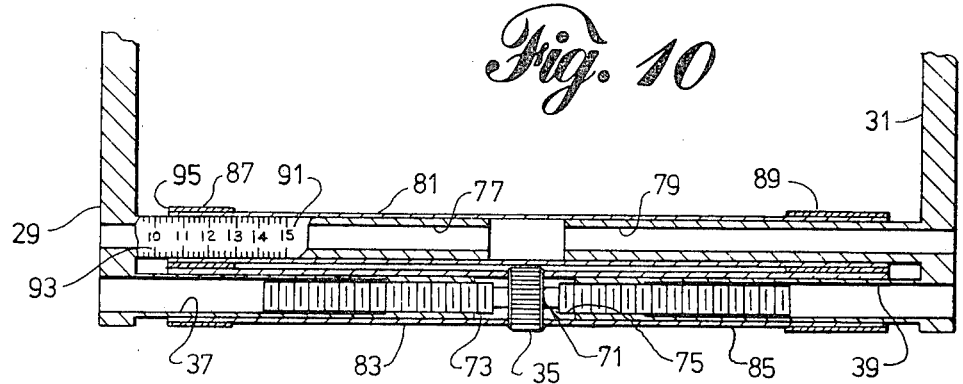
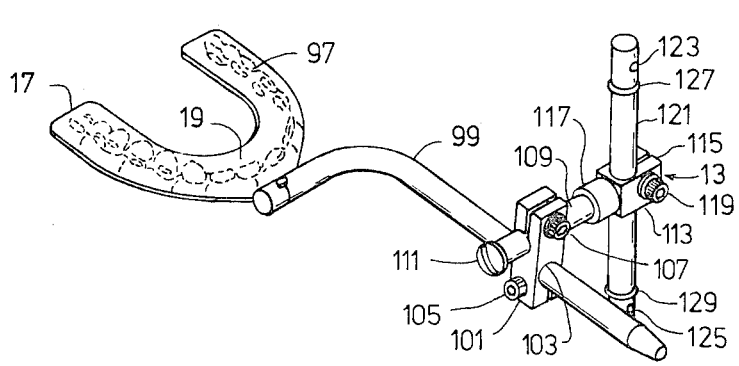

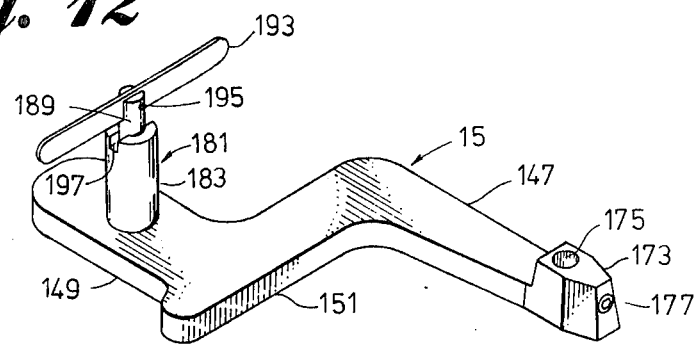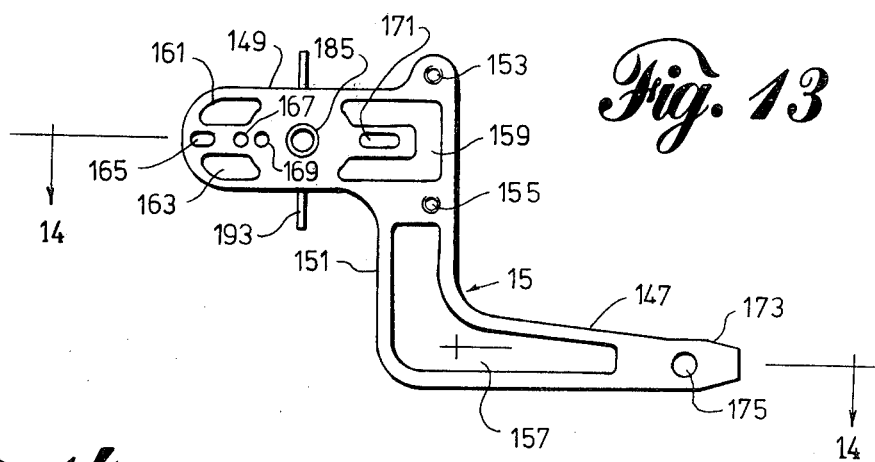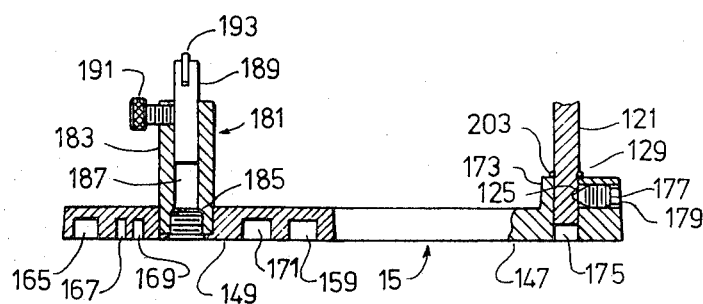

DENTAL FACE BOW

This invention relates to a dental face bow which is useful to record relationships between a dental patient's dentition and parts of his skull and jaw structure, and to transfer such to a dental articulator. More particularly, this invention relates to a readily fittable or positionable dental face bow wherein contact members thereof may be easily adjusted to position against a patient's head at a desired location by straight line movement of such contact members toward or away from each other in response to rotation of a part of a telescoping moving component of the face bow.

Dental articulators have been employed in the design and finishing of prostheses to help improve the fitting thereof and to make them compatible with various human jaw movements. Dental face bows have also been employed to record and/or measure certain characteristics of a patient's dentition so that such characteristics can be accurately transferred to a dental articulator. However, before the present invention such face bows could not be as easily fitted to the patient by the dentist or dental technician. Additionally, various advantages of parts of preferred face bows of this invention were not hitherto attainable nor was the fixing in position of a bite plate with respect to the face bow and the articulator as easily and accurately effected.

A search for prior art which might be relevant to the present face bow invention was conducted in U.S. subclasses 32-14D; 32-19; 32-20; 32-21; and 32-32. Also trade literature known to the inventor was reviewed. As a result of such search it was concluded that the most relevant patents are U.S. Pat. Nos. 1,052,806; 1,188,416; 1,402,225; 1,497,259; 3,084,438; 3,130,494; 3,218,716; and 4,084,319. Among the literature items showing mechanisms for fitting face bows the most relevant appear to be a circular issued by Denar Corporation, entitled *New Denar Slidematic Facebow* (which is undated but apparently was issued in early 1979) and a booklet of Whip-Mix Corporation entitled *Instructions for the Use of the Whip-Mix Articulator and Quick Mount Face Bow* (undated, but received in 1973). The facebow described in the Denar circular is also illustrated in U.S. Pat. No. 4,261,696, issued on Apr. 14, 1981.

The face bow illustrated in the Denar leaflet and the corresponding patent permits straight line movements of ear pieces together but such movement is in response to the pressing of face bow parts together by the dentist, technician or patient, and such movement is not as easily controllable as that of the present face bow. Also, the face bow of the leaflet utilizes a gear-tracks mechanism, in which there is usually more play than in applicant's device and such play is undesirable and adversely affects the use of the face bow. Furthermore, applicant's face bow will maintain his contact members in the same relative position until the thumb wheel or equivalent rotatable part thereof is turned, but the other mentioned face bow will not do this. Thus, the Denar device requires a locking mechanism, which is not needed in the face bows of the present invention. Several of the cited patents also show rack and gear movements, slides and telescoping or similarly operating parts but none shows a thumb wheel operated threaded telescoping mechanism for readily and controllably moving the face bow ear pieces together or apart in a straight line.

In accordance with the present invention a dental face bow comprises a pair of ear pieces for fitting the external auditory meatuses of a dental patient, a pair of temple arms, to each of which an ear piece is held, threaded telescoping means for simultaneously moving the temple arms and the ear pieces nearer together or farther apart, as desired, in a straight line path, in response to rotation of a part of such telescoping means, which telescoping means include a rotatable externally threaded internal member having a thumb wheel at a middle part thereof, with right handed and left handed external threads at end parts thereof, and matchingly internally threaded external tubular members about sides of said externally threaded parts and held to the temple arms, which internally threaded members simultaneously move together or apart, as desired, moving the temple arms with them, in response to the movement of the thumb wheel, and auxiliary telescoping means parallel to the threaded telescoping means and joined to the temple arms, so as to prevent relative rotation of such arms. Also within this description are: a particular type of ear piece; a face bow including finger guides, which, in some embodiments, are replaceable by facia rods; transfer means, used to hold a dental bite plate in desired position on the face bow and also to hold such bite plate in position on an articulator, which transfer means includes special means for accurately fastening it in place and means to aid in positioning it for fastening; and a universal jig for mounting the bite plate and transfer means on any of a plurality of articulators.

The invention will be readily understood from the present specification and the following detailed description, taken in conjunction with the drawing, in which:

FIG. 7 is a partially disassembled isometric view of the face bow of this invention;

FIG. 8 is a front elevational view of the face bow in closed position and joined to the top of the transfer rod;

FIG. 9 is a partial vertical sectional view along plane 9—9 of FIG. 8, showing the joinder of the face bow to the transfer rod;

FIG. 10 is a horizontal sectional view of a part of a complete bow, along plane 10—10 of FIG. 7, with selected portions thereof shown in top plan;

FIG. 11 is an isometric view of an transfer rod - bite index assembly;

FIG. 12 is a top front isometric view of a universal mounting jig of this invention;

FIG. 13 is a bottom plan view of the mounting jig; and

FIG. 14 is a longitudinal central vertical sectional view of said mounting jig along planes 14—14 of FIG. 13.

Figure 1:
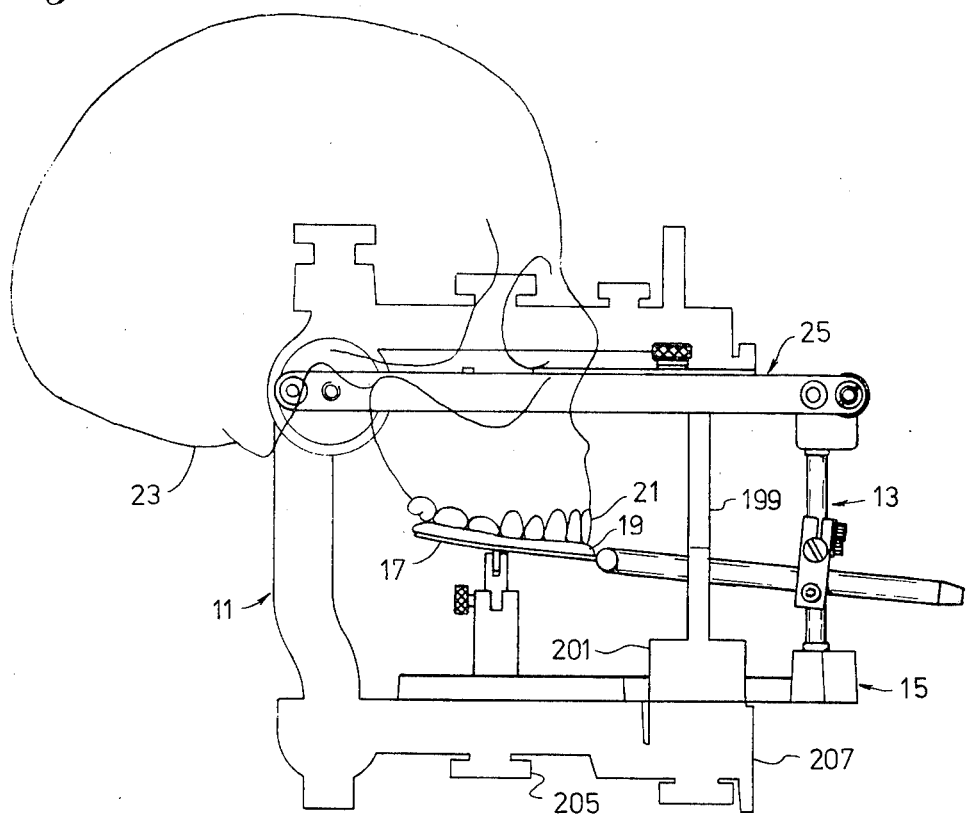
FIG. 1 is a side elevational view of a transfer rod - bite index assembly attached to a mounting jig and an articulator, with a corresponding view of a patient's skull and dentition and a face bow overlaid thereon, and with the facebow also being joined to the transfer rod.

In FIG. 1 a dental articulator 11 is illustrated, with a transfer rod - bite index assembly 13 mounted to it by means of mounting jig 15. To illustrate the relationship of the bite index assembly and bite plate 17 and impression material 19 thereof to dentition 21 and skull 23 of a dental patient, and to a face bow 25 of this invention held in place on the head of such patient the skull and the face bow are shown in FIG. 1, with the transfer rod - bite index assembly also being joined to the face bow. However, in normal use in accordance with this invention the transfer rod - bite index assembly will initially be fastened to the face bow and subsequently will be transferred to the articulator, but will not be held simultaneously by both such members. Because details of the constructions of the various apparatuses and components of FIG. 1 will be recited more specifically with respect to discussions of FIGS. 4 and 7–14, such details will not be further discussed herein with respect to FIG. 1. Similarly, the numerals identifying portions of FIGS. 2, 3, 5 and 6 primarily identify only the larger components of the assembly shown in FIG. 1 and descriptions of the parts thereof in more detail will be found in the more specific descriptions of FIGS. 4 and 7–14.

In FIG. 7 face bow 25, shown partially disassembled for better illustration thereof, includes: a pair of contact members 27, which are illustrated therein as ear pieces for fitting to the external auditory meatuses of a dental patient; supports 29 and 31, each of which supports one of the contact members; and threaded moving means 33, which means are capable of simultaneously moving the supports and the supported contact members nearer together or farther apart, as desired, following a straight line path, in response to rotation of a part of the moving means, such as thumb wheel 35, which, as will be shown later, upon rotation, rotates attached or integral oppositely threaded rod sections to move internally threaded parts 37 and 39 with respect to such rods, thereby opening or closing the face bow. Instead of (or in addition to) ear pieces 27, the face bow may have joined to it facia rods 41, each of which is for positioning against an anatomical posterior land mark known as the "hinge axis" of the tempormandibular joint, instead of in an external auditory meatus. Also held to the temple arm supports 29 and 31 of the face bow 25 are finger pieces 43, each of which has a concave depression 45 in an exposed circular face thereof so as to fit a finger tip and thereby to facilitate the patient gently pressing his fingers, usually his index fingers, against such depressions, to help fit the ear pieces into his external auditory meatuses. On temple arm 29 there is present an orbitale pointer 47, which is linearly and rotatably adjustable so as to have the rounded point portion 49 thereof in contact with an anterior patient land mark which is known as the orbitale. It is considered that when the patient's head is erect and he is looking straight ahead a line or plane drawn between the external auditory meatuses (or porions) and the orbitales will be horizontal (the Frankfort horizontal plane) and so such can be used as a base for orienting the bite index in a dental articulator. Such orientation is effected after impressing the patient's dentition against impression material on a bite plate while the bite index is fastened to an oriented face bow held aligned with the external auditory meatuses or the hinge axis of the temporomandibular joint, as a posterior location, and the orbitale, as an anterior location. Details of the various parts previously mentioned, the ear pieces, the facia rods, the finger pieces, the orbitale pointer, and associated parts of the face bow will now be given, after which the threaded moving means for positioning the posterior portion of the face bow on the head will be described in detail, in conjunction with FIGS. 8–10.

In suitable openings (not shown) at the posterior ends of the right and left temple arms 29 and 31 (right and left being with respect to the patient) are joined ear rods or tubes 51 which preferably include axial openings or passageways 53 for communicating ambient air pressure with the patient's ear when the face bow is in place on the patient. Ear pieces 27 also preferably include a communicating axial opening 55 for completing the directly venting passageway. The cross-sectional area of such direct passageway, through both the ear tubes and ear pieces, is preferably in the range of 0.8 to 5 sq. mm. and more preferably is of 1 to 3 sq. mm., e.g., 2 sq. mm., corresponding to circular bores of 1 to 2.5 mm. diameter and 1.1 to 2 mm., e.g., 1.5 mm., respectively. Ear pieces 27 may be suitably held to ear rods or tubes 51, as by threads, which are illustrated. It will be noted that the ear pieces are contoured to fit the external auditory meatus of the patient comfortably. It has been found that a rounded or domed surface of revolution shape is most desirable. Also, the material of construction of the ear pieces is preferably thermally non-conductive and sterilizable. Nylon and polypropylene, both of which can also be easily molded and threaded, are acceptable for such use.

Although it is highly preferable to utilize vented ear pieces, such as those shown, in establishing a posterior location for orientation of the face bow, alternatively, facia rods 41 may be utilized instead, which rods will normally be fitted to or placed against the hinge axis of the patient's temporomandibular joint. Such location is twelve millimeters forward of the external auditory meatus, a dimension indicated by a in FIG. 7. Openings 57 in the temple arm are adapted to receive facia pieces 41, when such are to be employed. Such openings may be threaded to accommodate threaded facia rods, as shown, but other means of joining such rods to the temple arms may also be employed. Finger pieces 43 are desirably held in the same openings intended for facia rods 41. They may have threaded extensions, as shown for the facia rods, or may be otherwise suitably fastened in place on the temple arms. Preferably, they will also be located about the distance a anteriorly of the ear piece locations. Although the finger pieces may be employed when the facia rods are present, with both being threaded into the same threaded openings, usually the finger pieces are most useful when insertion of the ear pieces into the external auditory meatus is utilized to establish a posterior orienting position for the face bow. When the ear pieces are being employed the facia rods will not normally be used.

As indicated in the drawing, orbitale pointer 47 is mounted on the right temple arm, although it could as readily be mounted on the left temple arm, or a pair of such pointers could be utilized. Pointer 47 includes a point portion 49 and an elongated slot 59. The pointer assembly includes a knurled-head screw 61 threadedly fitted into a threaded opening, not shown, in temple arm 29, and holding the pointer tightly against the upper surface 63 of such temple arm with the aid of a helical spring 65 (FIG. 8) and a nylon or other suitable washer 67 (FIG. 8). Dowel or stub pin 69, in a hole (not shown) in temple arm 29, is of a diameter so that it snugly fits between the walls of longitudinal slot 59 and thereby holds the pointer 47 in place in a safe storage position when screw 61 is tightened. When such screw is loosened some resisted vertical movement is possible because of the presence of spring 65 so that the pointer 47 may be lifted upwardly past the end of dowel 69, rotated and moved longitudinally to desired position, whereby end 49 thereof may be in contact with the patient's face at the orbitale, at which location the screw may be tightened so that the pointer may be fixed with respect to such location. It is noted that the presence of the spring 65 causes pointer 47 to be held in a position against the top surface 63 of temple arm 29 during any adjustments thereof and thereby prevents any excessive play or wobble and resulting changes of position during tightening of screw 61. A dowel like that indicated at 69, and a threaded hole into which screw 61 may be screwed may alternatively or additionally be provided at appropriate locations on left temple arm 31 or any corresponding such supporting member which may be part of a face bow of this invention so that, if desired, the anterior orienting location may be one matched to a hinge axis or condylar joint on the left side of the patient's head. Of course, the same pointer assembly may be employed or two such could be used if that were thought to be advantageous.

The moving means 33 for simultaneously, symmetrically and equally moving the temple arm supports and the supported contact members nearer together or farther apart, as desired, in a straight line path, operated by rotation of a readily rotatable part thereof, such as thumb wheel 35, includes a threaded rod (or drive screw unit) 71 (see FIG. 10) having threaded sides or end portions 73 and 75, with 73 being threaded with a right hand thread and 75 being threaded with a left hand thread. Thumb wheel 35 is positively held to the drive screw, as by a set screw, but may be integral with the drive screw, if desired. Drive screw 71, with thumb wheel 35 thereon, may be integral (with or without the thumb wheel) or may be made from several pieces, which may be assembled and held together by means of a thumb wheel set screw (not illustrated). For example, an inner end (near the thumb wheel) of one of the drive screws may be hollowed out, an inner end of the other may be turned down so as to be insertable in the first end, a set screw receiving hole may be drilled through both drive screw parts and tapped, and the thumb wheel set screw may be the means for holding all three parts together.

The drive screw, which may also be referred to as a rotatable internal threaded member (threaded externally), having a thumb wheel at a middle part thereof, fits within a pair of matching internally threaded internal tubular members. The internally threaded tubular members 37 and 39 are fastened respectively to temple arms 29 and 31 near anterior ends of said arms. Thus, when the temple arms are maintained relatively fixed with respect to rotation about tubes 37 and 39, rotation of thumb wheel 35 causes translational movements of threaded tubes 37 and 39 and of the temple arms. Rotation of the temple arms with respect to the internally threaded tube is prevented by telescoping tubes or rods 77 and 79, which are joined to temple arms 29 and 31, respectively, and which telescope inside tube 81, which is of an internal diameter slightly larger than the external diameters of tubes (or rods) 77 and 79. Additionally, tubular covers or guides 83 and 85 similarly are sized so as to have tubes or rods 37 and 39 fit therein in telescoping relationship and guides 81, 83 and 85 are each held at ends thereof to aligning members 87 and 89. Aligners 87 and 89 are preferably of synthetic organic polymeric plastic material, such as nylon or other thermoplastic, but also can be of metal or alloys. They are tightly joined to the external tubes or guides 81, 83 and 85, thereby holding the auxiliary telescoping means, comprising tubes 77, 79 and 81, and the telescoping moving means 33, parallel to each other and in a fixed relationship (although both are separately capable of telescoping). The aligners help to hold the face bow together without excessive play between the telescoping parts and perform other desirable functions, as will be apparent later, but a useful face bow of this invention can be made without them. Similarly, such a face bow can also be made omitting the auxiliary telescoping means provided that relative rotational movements of the temple arms are inhibited by other means, such as by brackets joined to the tubes and arms.

In FIG. 8 thumb wheel 35 is shown centrally located with respect to the temple arms, the distance from its midpoint to each temple arm being b when the telescoping moving means is in most closed position, as illustrated in FIG. 8. Although such position is the most efficient and is preferred, it is possible to locate the thumb wheel nearer to one temple arm than the other. As is seen from the drawing, especially FIG. 7, as the thumb wheel is moved, the distance between the temple arms and correspondingly, the distance between the ear pieces, will be changed. The distance between the ear pieces corresponds to or may be related to the intercondylar measurement of the patient's head and a dental articulator intercondylar setting. Such distances may be inscribed on a suitable part of the moving member of the face bow, such as telescoping tube 77, as at numerals 91 and measurement lines 93. Thus, when a pointer (not shown) or other part of a telescoping element, such as side wall 95 of alignment member 87, covers some of the numerals and markings, the dentist or technician may read off the intercondylar distance from the calibrated telescoping member. Such measurement may then be used to set the articulator for the desired intercondylar distance. Of course, when the articulator is a comparatively simple one in which a typical intercondylar distance is assumed and it is not possible to set this to improve the accuracy of the instrument, the present face bow can still be employed to set the bite index so that it is mounted in correct location on the articulator. The intercondylar distance inscriptions could also be on any of tubes 79, 37 or 39.

The bite index of the present face bow is very preferably held from aligning means 89, which is located to a side of the centrally positioned thumb wheel. Such location has been found to be most convenient so that the generally U-shaped bite plate may be centrally positioned and so that the bite index may be transferred to a universal jig adapted to fit any of a plurality of articulators without having a portion of the articulator obstruct the jig or a part of the index. The bite index could also be mounted to any other suitable face bow part, such as aligner 95, and tubes 81, 83 or 85. The particular preferred jig of this invention, as illustrated in FIGS. 12-14, is of a stylized squared S or Z shape, depending on viewing direction, with two essentailly parallel sides connected by a mid- or cross-member at right angles to them. However, other jig structures may be employed, although they may not be as adaptable to various articulator designs, and if the bite index is mounted on other aligning means, centrally located or otherwise, the jig will be adapted accordingly.

Figure 4:
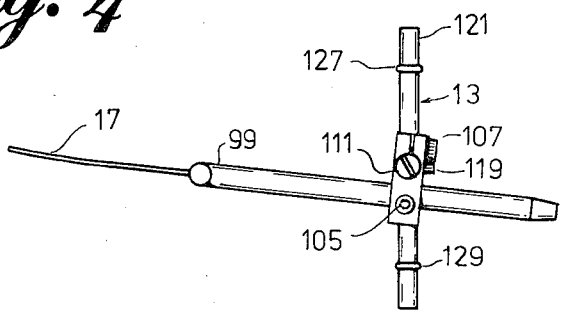
FIG. 4 is a side elevational view of the transfer rod - bite index assembly of FIGS. 1-3.
Figure 2:
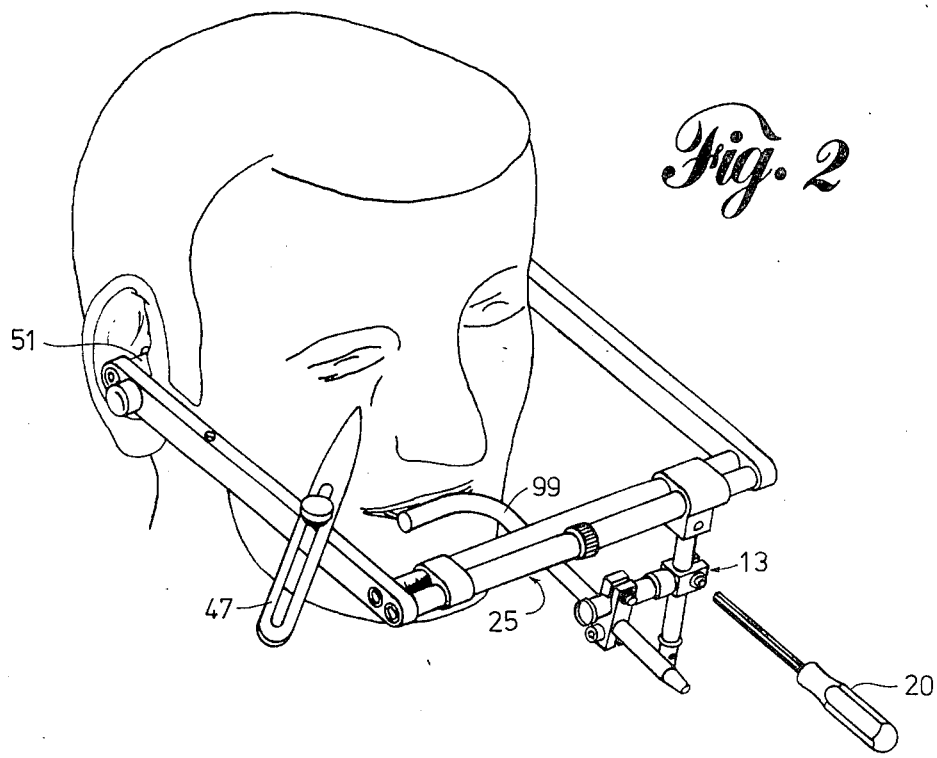
FIG. 2 is an isometric view of a face bow of this invention held in position on a patient.
Figure 3:
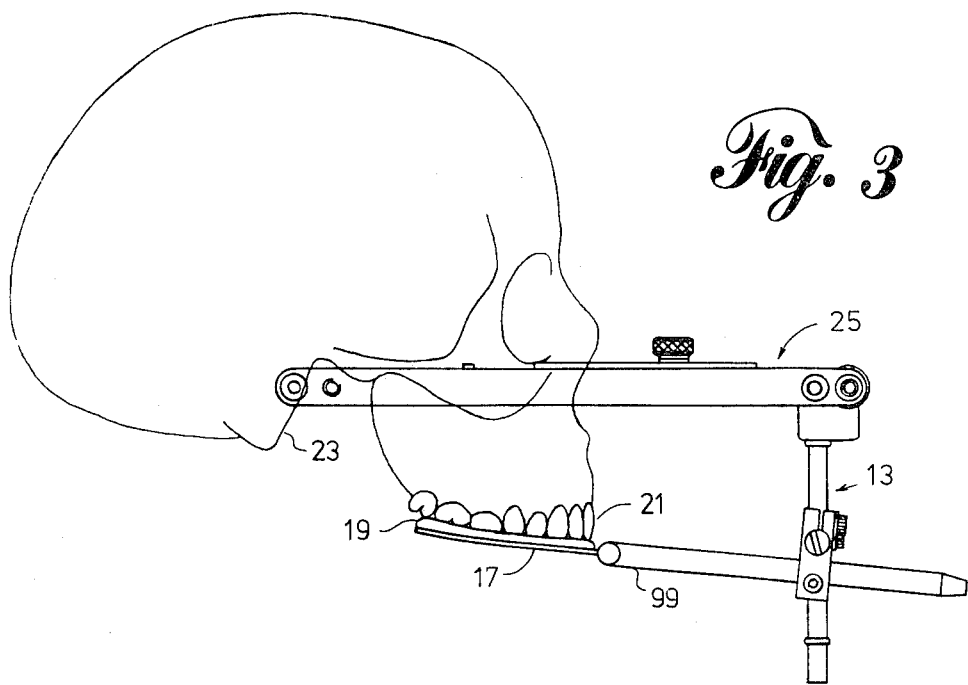
FIG. 3 is a side elevational view of the face bow of FIGS. 1 and 2 shown in relation to the skull and dentition of a patient.
Figure 5:
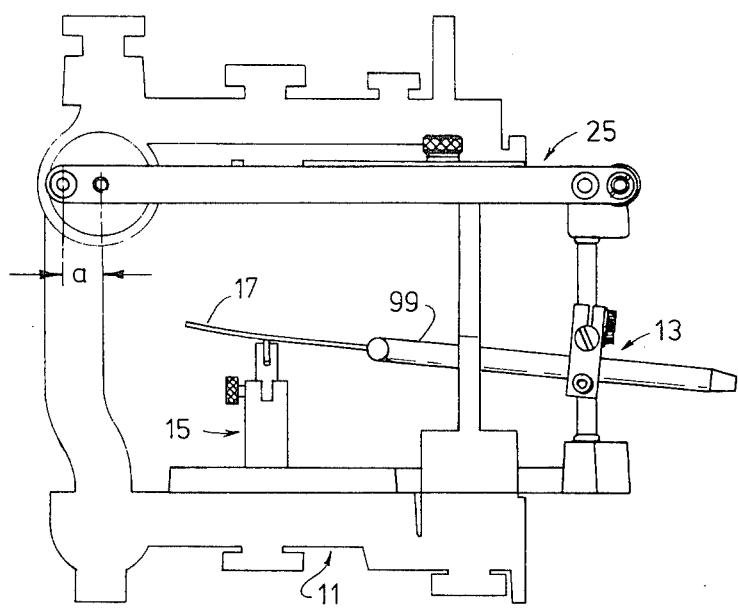
FIG. 5 is a side elevational view of the transfer rod - bite index assembly attached to the articulator of FIG. 1 by means of a mounting jig, with the corresponding position of the face bow also being illustrated.
Figure 6:
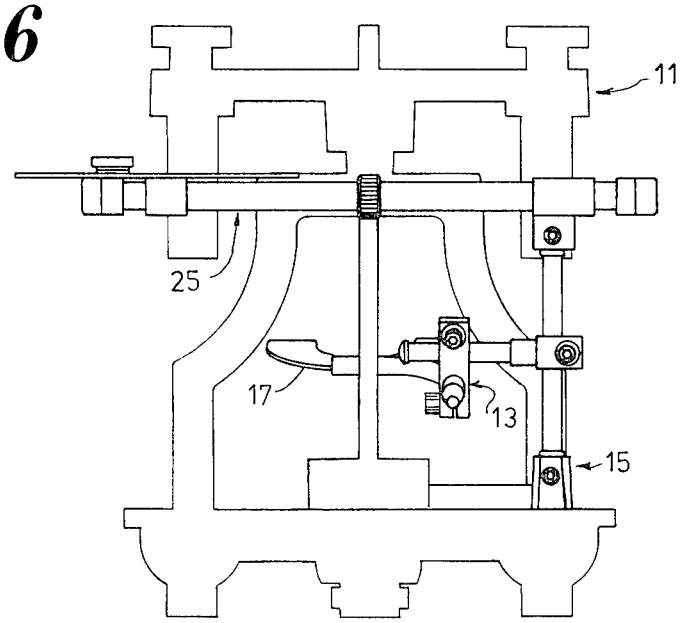
FIG. 6 is a front elevational view of the assembly of FIG. 5.

As is shown in FIGS. 4 and 11, bite index-transfer rod assembly 13 includes a bite plate or carrier 17, shown with impression material 19 on it in FIG. 11, with a dentition impression 97 therein, to which bite plate there is joined an L-shaped extension rod 99, bent so that its longer leg extends parallel to the patient's sagittal plane. (The combination of the bite index and the transfer means, less the bite plate and impression material, may be called the mounting means for the bite plate). Clamping member 101, which acts like a collet, includes a closable opening 103 adapted to have rod 99 inserted therein, with tightening screw 105, fitted in a corresponding threaded opening, not shown, being capable of drawing together split or slotted portions of the clamping member so as to hold rod 99 and bite plate 17 in fixed position therein, after adjustment. In a similar manner screw 107 may be adjusted to loosen or tighten a corresponding opening about transverse rod 109. Thus, by loosening screws 105 and 107 an essentially universal adjustability is possible between bite plate 17 and transverse rod 109. Also, the bite plate and the extension rod holding it may be moved forward, with respect to the patient, or backward (toward him), as desired, and the clamp 101 may be moved similarly transversely with respect to the transverse rod. Note that screw head 111, which is larger in diameter than rod 109, acts as a stop to prevent withdrawal of bite plate clamp 101 from transverse rod 109. At the other end of rod 109 there is present transverse clamp 113, which includes a clamping portion 115 and a collar portion 117, held to it. Clamp screw 119 may be loosened to allow vertical movement of the bite index with respect to transfer rod 121, about which clamp 113 is mounted, and tightening of screw 119 holds transverse clamp 113 in position with respect to the transfer rod. Of course, transverse clamp 113 may also be rotated about the axis of transfer rod 121. Tightening and loosening of screw 119 and other such clamp screws and set screws may be effected with an appropriate tool, such as screwdriver 20, as shown in FIG. 2.

Transfer rod 121 includes conically walled openings 123 and 125, near ends thereof, and elastic O-rings 127 and 129 near such openings and in the direction of the transverse clamp from such openings. The structures of such openings and rings, means for holding the rings in position, and the functions thereof will be more readily apparent from a review of FIG. 9 and the following description.

In FIG. 9 it is indicated that the angle between the temple arm axis and the axis of the transfer rod is 90°. Similarly, in FIG. 8, it was shown that the angle between the transfer rod axis and the axis of the moving means for telescopingly opening and closing the face bow is 90°. Temple arm 31 has held to it guide cylinders 79 and 39, the latter being internally threaded to fit drive screw portion 75. The unsectioned spacing between rod 75 and tube 39 in FIG. 9 represents the intermeshing threads thereof. About tubes 79 and 39 are guide tubes 81 and 85, respectively. The guide tubes are in telescoping relationship with one another and serve as auxiliary telescoping means parallel to the threaded telescoping means and joined to the temple arms, so as to prevent relative rotation of such arms. About the guide tubes is guide 89, firmly holding the guide tubes in position with respect to each other. Guide 89, unlike guide 87, includes a lower body portion 131 in which there is drilled and tapped hole 133, containing a set screw 135, which has a conically shaped forward point 137. When set screw 135 is tightened in position it snugly fits an opening 139 in transfer rod 121, which opening includes a conically shaped wall 141, matching the cone point of the set screw. Thus, by tightening the screw 135 a perfect and readily reproducible alignment of the transfer rod and the face bow is attained. To facilitate ready location of the hole by the screw, transfer rod 121 is provided with annular channel 143 into which an O-ring 127 fits. In a similar manner O-ring 129 (see FIG. 11) is held in another annular channel, not illustrated. The O-rings perform two very useful functions. First, they maintain a relationship between the bite index and the transfer rod by preventing release of the bite index from the rod even when clamp screw 11 is in loosened mode. More important, they allow entry of the transfer rod into bore 145 in aligner 89 so that when extended the fullest permissible distance, tightening of screw 135 will find the rod at the right height for alignment of the screw point with conical opening surface 141 of the transfer rod. Even if the height should be off slightly the resilience of the O-ring will permit adjustment as the screw is tightened. Furthermore, because openings 123 and 125 are in alignment longitudinally on the transfer rod, when fastening the rod to aligner 89 by tightening of screw 135 opening 125 (see FIG. 11) will be visible, facilitating accurate alignment of the transfer rod and the aligner. The importance of proper alignment of aligning openings 123 and 125 of transfer rod 121 and the importance of the trueness of such rod and accurate mating thereof with the face bow 25 by fitting in bore 145 of aligner 89 and also with respect to the mounting jig, the parts of which will now be described, to facilitate ready transfer of the bite index from the patient and face bow to an articulator, will be apparent from the following description.

In FIGS. 12–14 universal mounting jig 15 is shown in preferred squared S or Z shape, with parallel legs 147 and 149 and a connecting part 151. As is better seen from FIGS. 13 and 14, the under side of the mounting jig includes threaded openings 185, 153 and 155 for mounting on suitable articulators. Circular openings 167 and 169 and elongated depressions 165 and 171 are provided for accepting dowel locations of various articulators for alignment of the mounting jig for precise orientation of the transfer rod-bite index assembly. Openings are also provided at locations 157, 159, 161 and 163 to reduce the weight of the mounting jig. Openings 167 and 169 may also be threaded to assist in affixation of the jig to an articulator and it is within the invention to utilize other threaded openings and means for such fastenings and for correctly aligning the jig with the articulators. Similarly, the clearance openings may be varied in shape for particular purposes and the jig shape may be changed, although the form illustrated is considered best for fitting most commercial articulators and for avoiding conflicts with parts thereof. Instead of threading the clearance openings some may be left unthreaded and of such dimensions as to conform accurately with projections on the articulator so as to position and align the jig properly. Similarly, the clearance openings may be of other shapes than round (as shown) and still may conform and align with an articulator part, in conjunction with separate threading means, such as opening 185, adapted to be held to the articulator by a screw part thereof. Referring back to FIG. 12 and considering it in conjunction with FIG. 14, it is seen that at the end of leg 147 there is a transfer rod mount 173 which has an opening 175 therein, adapted to have transfer rod 121 inserted in it. Set screw 177 in threaded opening 179 has a conical point 203 which matches the walls of the conical opening 125 in the transfer rod and thereby, when tightened in place, aligns such rod. Thus, the bite index held by the transfer rod will be in desired relationship with the articulator, corresponding to its position with respect to the dentition of the patient, so that articulator movements of dental casts may be accurately simulated.

After positioning of the bite index and placement of a maxillary dental cast, the cast is mounted tightly with respect to the articulator, a procedure which will be described in more detail later. During such mounting a plaster or stone material is placed on the cast, in contact with an upper portion of the articulator so that when it hardens it will bind the two together in the relationship indicated by the impression in the impression material on the bite plate. Because the plaster or stone is heavy and the bite plate is normally thin and might be bent by the weight of the stone composition, a support for the bite index is provided on the jig. Support 181 is desirably adjustable, as shown, with respect to both height and inclination. The support 181 includes a cylinder 183, which is suitably held in place in base leg 149, as by sweating, pinning, soldering or welding, and which is internally threaded near the base thereof. Threaded porton 185 is adapted for being screwed to the articulator base 149 by means of an articulator screw 205 and by tightening thereof the jig and the supporting portion on it are tightly held in place on the articulator. Other threaded parts of the jig may be used to fasten it to articulators of other designs. Supporting cylinder 183 has a bore 187 therein in which slotted and pinned rod 189 may be moved vertically and then fastened in place by tightening of screw 191. Near the top of rod 189 is a pivotable member 193 which is adapted to serve as a support for a bite plate and stone or plaster bearing down on such plate. Supporting member 193 is pivoted about pin 195, which passes through the slotted end of adjustable rod 189. A provision for angling of member 193 is made in the slotting 197 of tube 183, so that in a lower position for supporting the bite plate, member 193 may still be tilted, when desired.

It will be noted that to obtain the desired relationships between various parts of the present apparatuses holding means will be periodically loosened and tightened. To simplify such operations the tightening means will normally be threaded screws and tightening may be by hand or with a screwdriver or Allen wrench. When the movement of the screws is to be effected in response to hand or finger movements the screws will preferably be knurled and of sufficient size to facilitate hand loosening and tightening. When changes in the screw positions require a tool that tool is preferably a screwdriver, which may be of the "Allen" type, and the screws may include heads with inset openings, usually hexagonal. The sizes of the screws will be similar, in most cases, and it will also be highly desirable to have the openings in the heads thereof identical so that a single tool can be used for making the adjustments.

Materials of construction of the present apparatus may be any of those normally employed in making apparatuses utilized in dental applications. Metals, alloys and natural and synthetic organic polymers may be employed. Thus, for example, the bite plate, temple arm, orbitale pointer and jig and the various tubes, rods, clamps and screws may be of stainless steel and/or aluminum or aluminum alloy in most cases (with the screws sometimes being of brass) but other metals and alloys may be substituted, in whole or in part. The ear pieces, finger pieces and aligners may be of suitable synthetic organic polymeric plastics, such as nylons, polypropylene, ABS, and polyacetals, or of other polymers, and the O-rings may be of neoprene, silicone rubber, polyurethane, natural rubber or other useful elastomers. The polymeric materials may replace metals for portions of the apparatus, for example, the temple bows, thumb wheel, orbitale pointer and mounting jig. In such instances the polymer will be chosen with care to assure that it will not warp, expand excessively or otherwise be dimensionally unstable so as to interfere with accurate use of the apparatus.

The operation of the present invention is simple and easy and the results obtained are accurate and reproducible. The invented face bow is responsive to slight movement of the thumb and adjustments are readily made and are held by the apparatus until the thumb wheel is moved. There is enough slight frictional effect due to the threaded engagement between the drive screws and the telescoping part to prevent unintentional bow movement. Thus, there is no adjustment maintaining screw that has to be tightened to hold the intercondylar distance constant during use of the face bow, so that there is no need for a third hand or for patient assistance in holding the bow in proper position for tightening. The present face bow may be employed to record the relationship between a patient's maxillary occlusal arch and his external auditory meatus and to provide for accurate transfer of such relationship to the opening axis of a dental articulator. Thus, an operator is provided with a means of relating the three-dimensional bite index of the patient's maxillary occlusal arch to his external auditory meatus. In the past such relationships could be obtained but in most instances it was necessary to send an entire face bow with the bite index fastened to it from the dental operatory to the dental laboratory. With the present invention the bite index, together with a transfer rod, may be removed from the face bow and may be sent to the dental laboratory without the face bow and yet, may be accurately fitted to an articulator of any of various types.

In use, the bite plate or bite plane is covered with wax or other suitable compound to a desirable thickness for obtaining an occlusal imprint of the patient's maxillary arch. The softened impression material on the bite plate is seated against the maxillary occlusal surface to create a distinct imprint without contact of the teeth with the metal of the bite plate. In a desired bite position the longer leg of the L-shaped stem attached to the bite plate will extend approximately parallel to the sagittal plane and will be at the patient's left. The operator will then take up the face bow and with it opened to approximately the fifteen cm. calibration mark, will assemble the transfer rod, the transverse clamp, the transverse rod and the bite clamp onto the face bow, with the transfer rod being oriented with respect to the face bow aligner so that tightening of the set screw in such aligner will properly position the transfer rod, and such screw is then tightened. Positions of the clamps and the transverse rod may be approximated but the clamps should be left somewhat loose for further adjustment when the bite clamp is installed on the stem attached to the bite plate. The face bow is then brought into position over the face of the patient so that the rod attached to the bite plate enters the opening in the loose bite clamp. Next, the thumb wheel is rotated so that the ear pieces enter and comfortably seat in the patient's external auditory meatus. The patient may assist the operator by applying his forefingers to the finger pieces or finger guides provided, so that adjustment of the face bow to final ear piece positions will be comfortable and so that the seating of the ear pieces will be secure. Following such operation the spring loaded thumb screw of the orbitale pointer is slightly released and the pointer is rotated to align its top surface with the patient's orbitale. Then, the clamp screws are tightened in the following order. First, the transverse clamp is tightened to the transfer rod, after which the bite clamp is tightened to the transverse rod and finally, the bite clamp is tightened to the stem attached to the bite plate. During tightening of the screws the face bow is held to offset any torquing movement being applied to the patient. Excessive tightening is not required and sometimes an initial light tightening while the face bow is in position on the patient may be followed by further tightening after it has been removed. The orbitale or a pointer may then be replaced in its storage position, the intercondylar width indicated is recorded (it is the center to center distance between the patient's condyles), the thumb wheel is rotated to release the ear pieces and the entire assembled bow is removed from the patient. Next, the tapered set screw is loosened and the transfer rod - bite index assembly is withdrawn from the face bow, after which it is carefully packaged with impressions or casts, interocclusal relation records and a notation of the patient's intercondylar width (if considered desirable), and sent to the dental laboratory.

In the dental laboratory the articulator is prepared for maxillary cast mounting by adjusting the incisal pin thereof, represented by numeral 199 in FIG. 1, and tightening the centric locks, after which the mounting jig is firmly attached in place to the lower member 207 of the articulator. The transfer rod - bite index assembly is then inserted at its lower end into the socket at the front of the mounting jig, with the tapered hole therein being aligned to accept the tapered set screw, which is then tightened to align the transfer rod by means of the tapered hole therein, and the rod is fastened in place. The support for the bite plate is then raised so as to contact the under side of the plate in appropriate position and the support is locked in place so as to enable the bite plate to carry the weight of the maxillary cast and the stone mounting medium. The maxillary cast is seated and luted into the occlusal index of the bite plane, after which the upper member of the articulator is swung back and a mixture of stone is placed on the cast. The upper member is then swung forward to imbed the mounting plate of the articulator and to bring the incisal pin into contact with the incisal guide, indicated generally at 201 in FIG. 1. After setting of the stone mounting the maxillary cast is disengaged from the bite plate, and the mounting jig and the transfer rod - bite index assembly fastened to it are removed. After positioning of the maxillary cast the mandibular cast is then mounted into centric in accepted manner.

Various modifications of the invention may be made without departing from it. Thus, for example, the shapes of the ear pieces, finger pieces, temple arms, orbitale pointer, jig and other parts may be changed so long as they operate in substantially the same manner as described. The telescoping parts, as previously mentioned, may be simplified. Instead of externally threaded drive screws, these may be interchanged with drive tubes which may be internally threaded. Although a thumb wheel, located as indicated, is highly preferred, its location may be changed and different means for rotating the drive screw may be employed, such as a handle, wrench or wheel communicating with an end of such screw. In any case it will normally be desirable to indicate a disengagement mark, similar to the intercondylar distance marks, to show when the threaded parts of the telescoping members may be accidentally disengaged if the face bow is opened too far. Such a warning mark is present in the face bows of this invention but is not specifically illustrated in the drawing. Lubrication openings may be provided to lubricate the drive screw but such are not necessary because if lubrication is desirable access to the drive screw is possible in the embodiment illustrated. Instead of the clamping means illustrated for holding the transfer rod to the bite plate rod other universal joint type connectors may be employed as parts of the bite index assembly. Also, while not as preferable, other indexing means may be utilized to assure that the transfer rod is properly aligned with the jig for the articulator, as well as with the face bow. Slip means or torque limiting clutches may be provided so that the torque transmittable by the thumb wheel may not exceed a certain amount, thereby limiting the forces pressing the ear pieces into the external auditory meatuses. Instead of O-rings other shapes of elastomeric materials may be held to the transfer rods as resilient stops, e.g., rounded end cylinders mounted in transverse holes in the rods. Various other modifications will be apparent to one of skill in the art reading this specification and viewing the drawing and these and the products resulting when substitutes for and equivalents of components are utilized are also within the invention.

Various advantages of the invention have already been described but several others will now be recorded. The employment of the venting ear pieces and ear rods allows conversation with the patient while the face bow is in position. Also, there is avoided the shock that would otherwise be transmitted to him if the metal portion of the face bow were to be accidentally struck by a metal implement during fitting. The offset jig position is also desirable, in conjunction with the shape thereof, which allows the use of the present invention with various articulators without obstruction. In particular, the offset location facilitates avoidance of contacts with the incisal guide and other central articulator parts.

What is claimed is:

1. A dental face bow comprising a pair of ear pieces for fitting the external auditory meatuses of a dental patient, a pair of temple arms, to each of which an ear piece is held, threaded telescoping means for simultaneously moving the temple arms and the ear pieces nearer together or farther apart, as desired, in a straight line path, in response to rotation of a part of such telescoping means, which telescoping means include a rotatable externally threaded internal member having a thumb wheel at a middle part thereof, with right handed and left handed external threads at end parts thereof, and matchingly internally threaded external tubular members about sides of said externally threaded parts and held to the temple arms, which internally threaded members simultaneously move together or apart, as desired, moving the temple arms with them, in response to the movement of the thumb wheel, and auxiliary telescoping means parallel to the threaded telescoping means and joined to the temple arms, so as to prevent relative rotation of such arms.

2. A dental face bow according to claim 1 wherein there are present tubular means covering at least part of the threaded telescoping means, and an internal telescoping part of the dental face bow is marked so as to indicate intercondylar distances, which correspond to distances between the ear pieces when they are fitted into patients' external auditory meatuses.

3. A dental face bow according to claim 1 which comprises means for holding a bite plate assembly, which means is mounted on a part of the telescoping means and/or auxiliary telescoping means, to a side of the thumb wheel so as to avoid interference with easy thumb or finger movement of said thumb wheel.

4. A dental face bow according to claim 1 comprising concavely faced finger guides located on the temple arms near the ear pieces and adapted to be contacted by the finger tips of a dental patient so that the patient may assist in guiding the ear pieces into positions in the patient's external auditory meatuses.

5. A dental face bow according to claim 4 wherein the temple arms have openings therein, the finger guides include portions insertable into said openings, and the openings are adapted to support facia rods together with or instead of the finger guides.

6. A dental face bow according to claim 1 wherein an orbitale pointer is horizontally movably positioned on one of the temple arms so that it can move in rotation and translation in a horizontal plane, and means are present on such arm for positioning the pointer and positively holding it in said position against the arm for safe storage when it is not being used.

7. A dental face bow according to claim 6 wherein finger guides are located on sides of the temple arms near the ear pieces and include concave faces adapted to be contacted by the finger tips of the dental patient so that the patient may assist in guiding the ear pieces into position in his external auditory meatuses.

* * * * *